United States Patent [19]

Shugar

[11] 4,444,185

[45] Apr. 24, 1984

[54] FIBEROPTIC TRACHEOTOMY METHOD

[76] Inventor: Martin A. Shugar, 3520 N. 30th Ter., Hollywood, Fla. 33021

[21] Appl. No.: 294,414

[22] Filed: Aug. 19, 1981

[51] Int. Cl.³ .............................................. A61F 17/32

[52] U.S. Cl. .................................. 128/305.3; 128/11; 128/397; 128/634; 128/200.26

[58] Field of Search ..................... 128/5, 6, 10, 11, 15, 128/16, 23, 305.3, 349 R, 634, 7, 8, 9, 303.1, 362, 395–398, 633, 200.26; 604/20, 27, 28; 350/96.26; 326/804

[56] References Cited

U.S. PATENT DOCUMENTS

| | | | |
|---|---|---|---|
| 2,212,334 | 8/1940 | Wallerich | 128/349 R |
| 2,991,787 | 7/1961 | Shelden et al. | 128/305.3 |
| 3,335,715 | 8/1967 | Hugenholtz et al. | 128/2 |
| 3,494,354 | 2/1970 | Yokota et al. | 128/6 |
| 3,674,013 | 7/1972 | Polanyl | 128/2.05 D |
| 3,809,072 | 5/1974 | Ersek et al. | 128/23 |
| 3,866,599 | 2/1975 | Johnson | 128/2 L |
| 3,881,468 | 5/1975 | Foltz | 128/23 |
| 4,050,450 | 9/1977 | Polanyl et al. | 128/2 L |
| 4,201,222 | 5/1980 | Haase | 128/634 |
| 4,212,304 | 7/1980 | Finney | 128/349 R |
| 4,244,362 | 1/1981 | Anderson | 128/200.26 |
| 4,248,214 | 2/1981 | Hannah et al. | 128/23 |

FOREIGN PATENT DOCUMENTS

| | | | |
|---|---|---|---|
| 2843553 | 4/1979 | Fed. Rep. of Germany | 128/6 |

*Primary Examiner*—Edward M. Coven
*Assistant Examiner*—Max F. Hindenburg

[57] ABSTRACT

A fiberoptic device that facilitates the performance of tracheotomies and a method for performing tracheotomies using that device. The device comprises a relatively short rigid tubular housing sealed at one end and connected at the other to a long tubular sheath. A bundle of optic fibers is contained in the sheath throughout its length. Light may be passed through the fibers and directed to a port near the sealed tip of the housing where it exits. The sheath has distance markings on its surface which enable a determination of the distance of the port to a point of observation within the markings. Also on the sheath is an alignment marking which enables the determination of the orientation of the port by observing the orientation of the alignment marking.

To use the device there must first be an endotracheal tube in place in the patient. An incision is made in the anterior portion of the neck and tissues in the vicinity of the trachea exposed. The device is then inserted into the endotracheal tube to the extent that the distance markings with relation to an appropriate reference point, such as the end of the endotracheal tube, indicate that the port is at the desired position. Light is then passed through the bundle of optic fibers, is emitted from the port and is seen by the surgeon through the exposed tissues. The surgeon is thereby directed to the proper location to complete the tracheotomy.

8 Claims, 3 Drawing Figures

29
31
7
9
21
23
5
3
27

FIBEROPTIC TRACHEOTOMY METHOD

BACKGROUND OF THE INVENTION

Tracheotomy, which means creation of an opening into the trachea such that one can visualize the interior of the trachea, is an ancient surgical procedure which is employed to stabilize a patient's airway (trachea) for a diverse number of reasons, such as acute and chronic respiratory failure, respiratory insufficiency, control of pulmonary secretions, following laryngeal and other head and neck trauma, and prior to many head and neck surgical procedures. In a vast majority of cases the procedure is performed electively with the patient anesthetized and an endotracheal tube in place. An endotracheal tube is a tube (today usually of plastic) of variable length and diameter with an inflatable cuff at the end of the tube. The endotracheal tube is inserted into the proximal trachea using a laryngoscope and is a temporary means of stabilizing the airway. In an elective tracheotomy, an incision is made in the lower neck in the mid line approximately 2 to 3 cm above the clavicles (collar bone). The incision is carried down through the subcutaneous tissues, the strap muscles divided, the thyroid isthmus divided, and then, using known anatomical relationships, the trachea is localized. The anterior aspect of the trachea is then freed of adjacent tissue and at this point an incision is usually made between the second and third tracheal rings thereby entering the trachea. A cuffed tracheotomy tube (again of variable size and length with a cuff) is inserted through the incision and the tracheotomy tube is then secured to the skin of the neck.

It is not uncommon to encounter a patient in which an anticipated tracheotomy would appear to be extremely difficult. This may be due to extreme obesity, a short bull (thick) neck, severe cervical arthritis, and following radiation therapy in which the skin is thickened and the known anatomical landmarks are distorted. In these cases a skillful anesthesiologist is usually able to pass an endotracheal tube into the trachea using a variety of techniques, thereby temporarily stabilizing the airway. It is customary in these difficult cases to get an anterior-posterior X-ray view of the neck to see where the air shadow of the trachea lies (these x-rays are frequently of limited value). At this point the surgeon will proceed ahead in the usual manner dissecting through the subcutaneous tissues, dividing the strap muscles and the isthmus of the thyroid at which point he must find the trachea. In these difficult cases the known anatomical relationships are distorted and this part of the procedure is most difficult. In most cases the surgeon will tediously dissect laterally searching for the trachea which can take a long time and still prove fruitless. In these cases a common practice is to take a 10 cc syringe with an 18 gauge needle and carefully aspirate where one thinks the trachea might be. If one actually has inserted the needle into the trachea then air will be aspirated and the location of the trachea will be ascertained. If one has inserted the needle into soft tissue, then air will not be aspirated. If one has inserted the needle into a vascular structure (the jugular vein or carotid artery) then blood will be aspirated. This technique, using a syringe and needle to locate the trachea, is clearly tedious, and generally unsatisfactory, but it has heretofore been one of the only methods available.

The use of fiberoptic devices is well known to the surgical arts. For example, U.S. Pat. No. 3,335,715 to Hugenholtz et al discloses a fiberoptic catheter comprising a multiplicity of flexible light-conducting fibers bundled together in a flexible sheath with a long and thin tip of pliable material spaced from the exposed light emitting and receiving face. The catheter of Hugenholtz et al is designed to be pushed through passages in the body for the purpose of illuminating and viewing the insides of such passages via the light-conducting fibers. The light is emitted and received along the same line as the longitudinal axis of the catheter.

U.S. Pat. No. 3,674,013 to Polanyl discloses a catheter similar to that of Hugenholtz et al except that the light emitting and receiving end of the fibers is at a right angle to the longitudinal axis of the catheter and that the tip of the catheter, which extends far beyond such end, has a permanent arcuate shape. The primary use suggested for the device of Polanyl is for observation inside parts of the body where it would be immersed in blood and it is designed to avoid thrombus formation, fibrin accumulation and "wall effects" which relates to unreliable readings of certain blood characteristics which the device is intended to measure. Such avoidance is supposedly at least partly achieved by having the light emitting and receiving face smoothly contoured into the side of the catheter, thus accounting for the light emitting and receiving end of the fibers being at the aforementioned angle.

There is other art which discloses fiberoptic catheters for use in the cardiovascular system. The device of U.S. Pat. No. 3,866,599 to Johnson permits observation of the inside of blood vessels and features an inflatable tip against which the circulating blood will exert sufficient force to pull the catheter into the desired location. The device of U.S. Pat. No. 4,050,450 to Polanyl et al effects inter-vivo testing of blood (e.g. measurement of oxygen saturation) by measuring amounts of diffuse reflection of light from a target medium, i.e. blood, and features attachments which permit calibration of the catheter and its associated electro-optic equipment. The device of U.S. Pat. No. 4,201,222 to Haase effects simultaneous measurement of blood gases, pressure and pulse rate. In the fiberoptic devices of the last mentioned three references the light is emitted and received along the same line as the longitudinal axis of the catheter.

I have discovered a fiberoptic device and method for using that device that facilitates and simplifies the performance of elective tracheotomies.

SUMMARY OF THE INVENTION

In one embodiment, my invention is a device for facilitating the performance of tracheotomies having the following elements: (a) an elongated tubular housing of rigid material, sealed at one end by an externally convex surface and open at the other end, having an aperture means in close proximity to the sealed end of the housing providing an outlet for light from the housing; (b) a longitudinally flexible tubular sheath resistant to torsional flexing of substantial length with one end attached to and in sealed communication with the open end of the housing and open at the other end, the exterior length of the housing and the exterior diameters of the housing and sheath being no greater than that which permits convenient insertion into and passage through an endotracheal tube; (c) a multiplicity of flexible light conducting fibers bundled together and substantially parallel to each other, the bundle being within and at least coextensive with the sheath, one end of the bundle being exposed as a light emitting face in a manner enabling the emission of light from the aperture means and the other end being exposed as a light receiving face, the length of the sheath and bundle of fibers being sufficient to enable convenient access of the housing through the endotracheal tube and as far as the desired position in the patient's trachea, and, at the same time, access of the opposite end of the device to a high intensity light source means which with the light receiving face of said bundle of fibers is placed in juxtaposition so as to enable direct exposure of the light receiving face to light eminating from the source; and (d) distance marking means fixed on the exterior surface of the sheath providing a means of measuring the distance from a desired point of observation on the sheath within the marking means to the aperture means.

In another embodiment, my invention is a method for performing tracheotomies. In this method the skin and subcutaneous tissues in the anterior portion of the neck are first incised and the strap muscles and thyroid isthmus are divided. A flexible elongated tubular fiberoptic device is then inserted down through an endotracheal tube which is at least partially transparent to visible light and which extends beyond the desired point of external entry into the trachea, the device capable of emitting high intensity light from an aperture means at the end inserted into the patient. The device has distance marking means on its exterior surface along its length enabling the determination of the distance from a point of observation on the device to the aperture means. The device is advanced into the proximal trachea an appropriate distance with reference to the aperture means depending on the patient's age, sex and height, the distance being measured from a fixed point of observation in the immediate vicinity of the distance marking means on the exterior surface of the device. The device is rotated in the endotracheal tube until the aperture means is positioned anteriorly to the patient's neck. The light source is turned on and it is observed through the exposed tissue of said patient, through which light is transmitted, the exact locus of the aperture means of the device from which light eminates, which is also the exact locus of the appropriate point of entry into said trachea. The tracheotomy is then completed through the point of entry.

In still another embodiment, my invention is another method for performing tracheotomies. The skin and subcutaneous tissues in the anterior portion of the neck of the patient are first incised and the strap muscles and thyroid isthmus are divided. A flexible elongated tubular fiberoptic device is then inserted down through an endotracheal tube inserted into the proximal trachea of the patient not as far as the desired point of entry into the trachea, the device capable of emitting high intensity light from an aperture means at the end inserted into the patient. The device has distance marking means on its exterior surface along its length enabling the determination of the distance from a point of observation on the device to the aperture means. The device is advanced into the proximal trachea an appropriate distance with reference to the aperture means depending on the patient's age, sex and height, the distance being measured from a fixed point of observation in the immediate vicinity of the distance marking means, on the exterior surface of the device and extending beyond the end of the endotracheal tube in the trachea. The device is rotated in the endotracheal tube until the aperture means is positioned anteriorly to the patient's neck. The light source is turned on and it is observed through the exposed tissues of the patient through which light is transmitted, the exact locus of the aperture means of the device from which light eminates, which is also the exact locus of the appropriate point of entry into the trachea. The tracheotomy is then completed through the point of entry.

Other embodiments of my invention are set forth in the following discussion and involve details such as the dimensions of the device, the construction of the device and techniques for its use.

DETAILED DESCRIPTION

The fiberoptic tracheotomy guide was devised to alleviate the problems encountered in localizing the trachea, particularly during the above discussed difficult tracheotomies. The device may only be employed with an endotracheal tube in place which will be the case in the great majority of elective tracheotomies performed.

Figure 3:
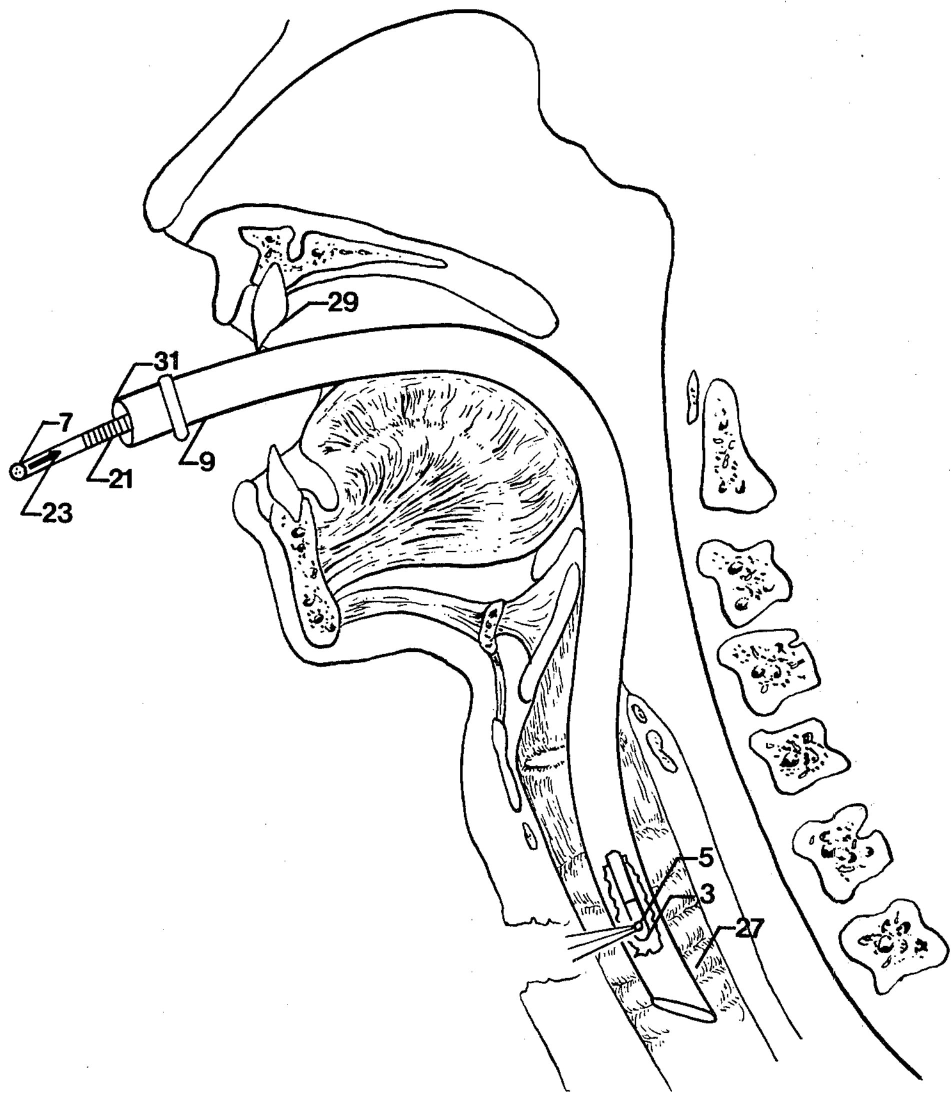
FIG. 3 gives a cross-sectional side view (sagittal) of a portion of a human head and neck, showing an endotracheal tube in place and the device of the present invention in place and operating in the endotracheal tube with the housing of the device viewable at a fragmentary cross-section of the endotracheal tube and a portion of the sheath shown exiting from the inlet of the endotracheal tube.

In the figures, housing 3 is shown with aperture means (hereinafter referred to as "port") 5 and in sealed communication with sheath 7. The housing is an elongated tube sealed at tip 8 by an externally convex surface and open at the other end for communication with the sheath. Sheath 7 is longitudinally flexible, but preferably resistant to torsional flexing so that when a portion of the sheath at a substantial distance from the housing is rotated about its longitudinal axis, the entire device, including the housing, will rotate in unison when the device is in place in endotracheal tube 9 as shown in FIG. 3.

The housing and sheath are most conveniently of substantially the same external diameters, and such diameters as well as the external length of the housing may be no greater than that which permits convenient insertion into and passage through the endotracheal tube when in place. In the typical adult these dimensions would be diameters of about 4 mm. and a housing length of about 1 cm. to about 2 cm. Port 5, unlike in the devices of the prior art, is in close proximity to tip 8, as close as possible while still allowing the port to function as hereinafter described.

Inside sheath 7 and substantially coextensive with it are a multiplicity of flexible light conducting fibers substantially parallel to each other and bundled together in bundle 11. End 13 of bundle 11, shown in FIG. 2 as extending into the housing is a light emitting face which emits directly into housing 3. The other end of bundle 11 is a light receiving face and is held in juxtaposition with high intensity light source means 15 so as to enable direct exposure of the light receiving face to light eminating from source means 15. The entire length of the device should be sufficient to enable convenient access of housing 3 through the endotracheal tube and as far as the desired position in the patient's trachea, and at the same time access of the opposite end of the device to light source means 15. Such length would be about 120 cm.

Figure 2:
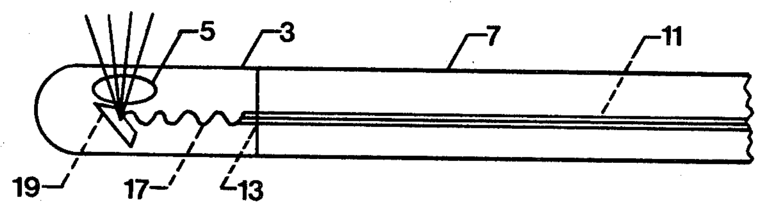
FIG. 2 gives a fragmentary cross-section view of the housing of the device and a portion of the sheath taken on line 1—1 of FIG. 1, partially rotated about the longitudinal axis of the device to show internal details of the housing and sheath internals.

The light eminating into housing 3 from end 13, shown as light beam 17, must find its way to port 5, which in turn must be of sufficient size to allow the escape of a substantial portion of such light. Light directing means in the housing effects the directing of light beam 17 to port 5. The light directing means is shown in FIG. 2 as reflecting surface 19 which is positioned inside housing 3, probably at an angle of 45° to the light, to reflect light beam 17 in a direction towards port 5. Unlike the devices of the prior art, the device of the present invention is capable of emitting and only need emit light. There are no means for viewing through the device the area illuminated by the light from port 5.

Port 5 is preferably a circular opening of at least about 1.5 mm. in diameter. The port is ideally sealed with a transparent solid material, flush with the exterior surface of the housing, to prevent the accumulation of nonsterile materials in the housing which might also interfere with the performance of the device. The sealing material might comprise a lens which would serve to focus the otherwise diffuse light eminating from port 5 into a narrow beam.

It is essential for the device of the present invention to have incorporated with it a measuring means that will enable the determination of the distance of a given point of observation on sheath 7 to port 5. The devices of the prior art give no hint to such measuring means. A skilled surgeon using the device will know, depending on the patient's age, sex and height, the distance from a visible anatomical landmark (such as the upper incisor teeth), or other fixed point of reference, to the point on the trachea where exterior entrance should be made, i.e. between the second and third tracheal rings, and will be able, via the measuring means, to insert the device that distance from the landmark into the patient. The measuring means comprises uniformly spaced distance markings 21 fixed on the exterior surface of sheath 7. Each marking in a preferred embodiment will intersect an imaginary reference line, shown as a dotted line in FIG. 1 on the surface of the sheath passing through a central point of the port or intersecting a straight line passing through a central point of the port and transverse to the housing, the reference line being parallel to the longitudinal axis of the sheath. Each marking will be a specific distance from port 5, and thereby enable the surgeon, by glancing at the marking nearest the landmark he is using, to know exactly how far the port is from such landmark.

With further regard to the distance markings, they are ideally parallel lines perpendicular to the above reference line, begin at about 10 cm. from port 5 and occur at 1 cm. intervals to 50 cm. from the port. Ideally, the markings will be numbered with the numbers fixed on the surface of the sheath adjacent to the markings to which they correspond. A given number will state the number of centimeters from port 5 of the marking associated with that number. It should only be necessary to have every fifth or perhaps only every tenth marking numbered.

It is very helpful for there to be an alignment marking means 23 (also not disclosed in the prior art), lying in the same above reference line, fixed on the exterior surface of sheath 7 at a position on the sheath proximate to the distance marking farthest from the housing. Thus, when housing 3 is out of sight within the patient, the surgeon may accurately point port 5 to the anterior region of the neck by rotating the sheath, until the alignment marking is pointed in that direction. The port will rotate with the alignment marking in view of the resistance of the sheath to torsional flexing. Alignment marking 23, which need only be a short line, is shown in FIG. 1 as an arrow, and is desirably about 60 cm. from port 5.

Figure 1:
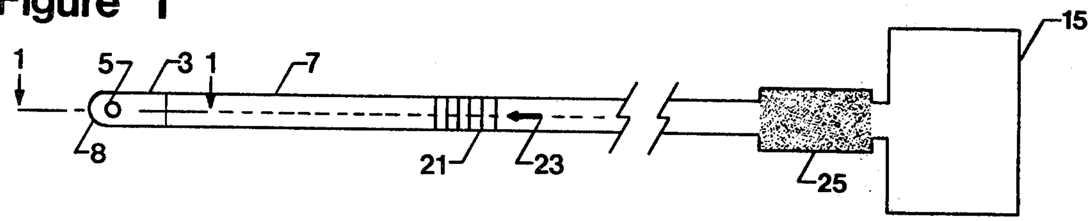
FIG. 1 provides a side view of a fiberoptic tracheotomy guide.

The device of the present invention is shown in a preferred embodiment in FIG. 1 with fitting 25 secured to the end of sheath 7 distal to housing 3. The bundle of fibers and light receiving face thereof extend into this fitting. The fitting is constructed so as to enable detachable coupling with light source means 15. Fitting 25 will thus enable the surgeon to quickly and conveniently attach sheath 7 to light source means 15 once the device is in place or is ready to be inserted into place in the patient.

The method of the present invention, which is limited to the performance of tracheotomies, is not even remotely hinted at by the prior art which discloses the use of fiberoptic catheters, only superficially similar to the device of the present invention, for blood analysis or observation into various body internal structures.

Referring to FIG. 3, endotracheal tube 9 is inserted in place into the proximal trachea 27 of the patient. The endotracheal tube when it extends into the trachea beyond the desired point of external entry must, of course, be at least partially transparent to visible light so that the light eminating from the device of the invention inside the tube may be seen from outside the tube. It is not essential, however, that the endotracheal tube be inserted into the proximal trachea of the patient as far as the desired point of entry into the trachea, in which case port 5 will extend beyond the end of the endotracheal tube in the patient. The surgeon some time after the endotracheal tube is in place, (usually seven to ten days thereafter) will proceed with the tracheotomy probably because it is not prudent medical practice to rely on an endotracheal tube to stabilize the airway for longer than the seven to ten day period in view of eventual damage that will occur to the tissues in contact with the endotracheal tube.

The surgeon will initiate the actual tracheotomy by incising the skin and subcutaneous tissues in the anterior portion of the neck of the patient and dividing the strap muscles and thyroid isthmus to expose the tissues that conceal the trachea but which are capable of transmitting light. The incision in the neck of the patient is shown in FIG. 3. The above described device of the present invention is then inserted down through the endotracheal tube and into the proximal trachea an appropriate distance with reference to the light emitting port. As mentioned before, the surgeon will know the appropriate distance from his observation of the physical characteristics of the patient. The distance is measured, using distance markings 21 on the exterior surface of the device, from a fixed point of observation, in the immediate vicinity of the distance markings, such as incisor teeth 29. The device is then rotated in the endotracheal tube until port 5 is positioned anteriorly in the patient's neck. Alignment marking 23 will facilitate such positioning by providing visible indication of the alignment of port 5 which is out of sight. In FIG. 3, port 5 and alignment marking 23 are shown rotated slightly from an anterior orientation in order that they may be seen in the figure.

The device is then coupled to light source 15 (not shown in FIG. 3) and the light source (commonly referred to as a light "fountain") is turned on and, preferably, the room lights dimmed. The surgeon is then easily able to see through the exposed tissues the light which eminates from port 5. This light precisely directs the surgeon to the trachea and the rest of the tracheotomy is performed in the routine fashion. It should be noted that when the fiberoptic device is inserted down through the endotracheal tube the anesthesia must be disconnected for a short interval of time which may safely be as long as two minutes. The localization of the trachea using the device of this invention can be performed in as quickly as 15 to 30 seconds.

Since endotracheal tube 9 usually will protrude out of the patient's mouth a certain distance as shown in FIG. 3, about 16 cm., for example, it may be difficult to use the incisor teeth as a point of observation or landmark in measuring the exact locus of light emitting port 5. In such case all the surgeon need do is use end 31 of endotracheal tube 9 as a point of reference and read the appropriate marking from distance markings 21 at that point. From that reading the surgeon will subtract the distance from incisor teeth 29 to end 31 and will thereby have calculated the distance from incisor teeth 29 to port 5.

I claim as my invention:

1. A method for performing tracheotomies comprising incising the skin and subcutaneous tissues in the anterior portion of the neck of the patient, dividing the strap muscles and thyroid isthmus, inserting a flexible elongated tubular fiberoptic device down through an endotracheal tube which is at least partially transparent to visible light and which extends beyond the desired point of external entry into the trachea, said device capable of emitting high intensity light from an aperture means at the end inserted into the patient and said device having distance marking means on its exterior surface along its length enabling the determination of the distance from a point of observation on said device to said aperture means, advancing said device into the proximal trachea an appropriate distance with reference to said aperture means depending on the patient's age, sex and height, said distance being measured from a fixed point of observation in the immediate vicinity of said distance marking means on said exterior surface of said device, rotating said device in said endotracheal tube until said aperture means is positioned anteriorly to the patient's neck, turning on said light source and observing externally from said patient's neck through the exposed tissues of said patient through which light is transmitted the exact locus of the aperture means of said device from which light eminates which is also the exact locus of the appropriate point of entry into said trachea, and completing said tracheotomy through said point of entry.

2. The method of claim 1 wherein said fixed point of observation is at the upper incisor teeth of the patient and said device is inserted into the endotracheal tube to the extent said aperture means is the desired distance from said incisor teeth as measured by said distance marking means.

3. The method of claim 1 wherein said endotracheal tube and the open end thereof extends out of the mouth of the patient a specific distance from the incisor teeth of the patient, said fixed point of observation being at said open end of said endotracheal tube with said device inserted into the endotracheal tube to the extent said aperture means is the desired distance from said open end as measured by said distance marking means.

4. The method of claim 1 wherein said device has an alignment marking on its exterior surface at a locus not out of sight within the endotracheal tube to enable determination of the alignment of said aperture means by observing the alignment of said alignment marking.

5. A method for performing tracheotomies comprising incising the skin and subcutaneous tissues in the anterior portion of the neck of the patient, dividing the strap muscles and thyroid isthmus, inserting a flexible elongated tubular fiberoptic device down through an endotracheal tube inserted into the proximal trachea of the patient not as far as the desired point of entry into the trachea, said device capable of emitting high intensity light from an aperture means at the end inserted into the patient and said device having distance marking means on its exterior surface along its length enabling the determination of the distance from a point of observation on said device to said aperture means, advancing said device into the proximal trachea an appropriate distance with reference to said aperture means depending on the patient's age, sex and height, said distance being measured from a fixed point of observation in the immediate vicinity of said distance marking means, on said exterior surface of said device and extending beyond the end of said endotracheal tube in the trachea, rotating said device in said endotracheal tube until said aperture means is positioned anteriorly to the patient's neck, turning on said light source and observing from a point external of said patient through the exposed tissues of said patient through which light is transmitted the exact locus of the aperture means of said device from which light eminates, which is also the exact locus of the appropriate point of entry into said trachea, and completing said tracheotomy through said point of entry.

6. The method of claim 5 wherein said fixed point of observation is at the upper incisor teeth of the patient and said device is inserted into the endotracheal tube to the extent said aperture means is the desired distance from said incisor teeth as measured by said distance marking means.

7. The method of claim 5 wherein said endotracheal tube and the open end thereof extends out of the mouth of the patient a specific distance from the incisor teeth of the patient, said fixed point of observation being at said open end of said endotracheal tube with said device inserted into the endotracheal tube to the extent said aperture means is the desired distance from said open end as measured by said distance marking means.

8. The method of claim 5 wherein said device has an alignment marking on its exterior surface at a locus not out of sight within the endotracheal tube to enable determination of the alignment of said aperture means by observing the alignment of said alignment marking.

* * * * *